United States Patent
Bonaventura et al.

(10) Patent No.: US 11,523,735 B2
(45) Date of Patent: Dec. 13, 2022

(54) FLEXIBLE HEADREST FOR OPHTHALMIC INSTRUMENT

(71) Applicant: Reichert, Inc., Depew, NY (US)

(72) Inventors: Russell J. Bonaventura, Williamsville, NY (US); James M. Schweitzer, Lancaster, NY (US)

(73) Assignee: Reichert, Inc., Depew, NY (US)

( * ) Notice: Subject to any disclaimer, the term of this patent is extended or adjusted under 35 U.S.C. 154(b) by 296 days.

(21) Appl. No.: 16/896,506

(22) Filed: Jun. 9, 2020

(65) Prior Publication Data

US 2021/0378503 A1 Dec. 9, 2021

(51) Int. Cl.
  *A61B 3/00* (2006.01)
  *A61B 3/16* (2006.01)
(52) U.S. Cl.
  CPC .............. *A61B 3/0083* (2013.01); *A61B 3/16* (2013.01)
(58) Field of Classification Search
  CPC ........... A61B 3/0083; A61B 3/10; A61B 3/16; A61B 8/10
  USPC ............................................ 351/206; 396/18
  See application file for complete search history.

(56) References Cited

U.S. PATENT DOCUMENTS

| | | | | |
|---|---|---|---|---|
| 3,199,426 A | * | 8/1965 | Kuwahara | A61B 3/14 351/206 |
| 2005/0137473 A1 | | 6/2005 | Kontiola | |
| 2007/0107733 A1 | * | 5/2007 | Ho | A61M 16/0622 128/206.24 |
| 2007/0163594 A1 | * | 7/2007 | Ho | A61M 16/0633 128/206.24 |

FOREIGN PATENT DOCUMENTS

| | | |
|---|---|---|
| EP | 2601993 B1 | 2/2018 |
| JP | 2001008897 A * | 1/2001 |

OTHER PUBLICATIONS

ICare Finland Oy, iCare ic100 Instruction Manual TA011-047 EN-1.0, 2015, pp. 4 and 6, Finland.
ICare Finland Oy, iCare ic200 Instruction Manual TA031-046 EN 2.6, 2018, pp. 5 and 9, Finland.

\* cited by examiner

*Primary Examiner* — Zachary W Wilkes
(74) *Attorney, Agent, or Firm* — Hodgson Russ LLP

(57) ABSTRACT

A headrest for an ophthalmic instrument facilitates fine positioning of the instrument relative to an eye of a test subject without the need to remove a contact element of the headrest from contact with the test subject's face. The ophthalmic instrument may be, for example, a rebound tonometer or a non-contact tonometer. The headrest includes a hollow bulbous contact element formed of resiliently deformable material, for example a thermoplastic elastomer (TPE) or silicone rubber. An outer surface of the contact element may have a spherical shape or a spheroidal shape when the contact element is not deformed.

7 Claims, 3 Drawing Sheets

FLEXIBLE HEADREST FOR OPHTHALMIC INSTRUMENT

FIELD OF THE DISCLOSURE

The present disclosure relates to ophthalmic instruments which are positioned relative to an eye of a test subject by an operator as a prerequisite to measuring an ophthalmic parameter of the eye. For example, the present disclosure relates to rebound tonometers which utilize a disposable probe for contacting a cornea of the eye to measure intraocular pressure (TOP), and non-contact tonometers which utilize an air pulse to temporarily deform the cornea to measure IOP.

BACKGROUND OF THE DISCLOSURE

A rebound tonometer is an ophthalmic instrument that propels a movable measurement probe in a controlled manner along a measurement axis toward the cornea of an eye to measure intraocular pressure. During a measurement, the probe contacts the cornea, decelerates at a rate which depends on intraocular pressure, and then rebounds in a direction away from the cornea back toward the instrument housing. The rebound tonometer detects the motion of the measurement probe and determines intraocular pressure based on the detected motion of the probe. For example, the measurement probe may have a magnetized shaft that travels within a coil in the instrument housing. The coil may be energized momentarily to propel the probe toward the cornea by electromagnetic force, and then, after energizing current to the coil is shut off, a current may be induced in the coil by the moving probe to provide a detectable voltage signal representing velocity of the probe as a function of time. Alternatively, two coils may be provided, wherein one coil is used to propel the probe and the moving probe induces current in the other coil to provide a measurement voltage signal. The voltage signal may be recorded and processed to determine a measured IOP value.

Proper three-dimensional positioning of the rebound tonometer relative to the eye is an important factor for IOP measurement accuracy and repeatability. Immediately prior to propelling the probe to commence an IOP measurement, the rebound tonometer is ideally positioned by the operator such that the measurement axis intersects the corneal apex while the test subject gazes directly along the measurement axis (X-Y alignment), and a rounded tip of the measurement probe is located at predetermined working distance (Z distance) from the corneal surface.

A non-contact tonometer, also referred to as an air-puff tonometer, is another type of ophthalmic instrument for measuring TOP. Like a rebound tonometer, a non-contact tonometer may be hand-held and manually positioned by an operator. Non-contact tonometers have a three-dimensional positioning requirement similar to that described above for a rebound tonometer, except that a fluid discharge tube for discharging an air pulse toward the eye defines the measurement axis and working distance.

Ophthalmic instruments of the types described above include a measurement head which carries the measurement hardware, and the measurement axis of the instrument extends from the measurement head. Where the ophthalmic instrument is a hand-held instrument manually positioned relative to the test subject, it is common to provide a handle extending downward from the measurement head. Although perfect or ideal three-dimensional positioning is impossible to achieve due to movement of the movement of the test subject and/or movement of the operator's hand holding the instrument, three-dimensional positioning within an acceptable tolerance range relative to the ideal position is a prerequisite to obtaining a reliable measurement result.

To assist an operator in positioning the instrument relative to a test subject, it is known to provide a headrest which projects forwardly beyond a front portion of the measurement head at a location spaced vertically from the measurement axis, wherein the headrest includes a contact element at its front end for contacting the face of the test subject. Where the headrest is located above the measurement axis, the contact element contacts the forehead of the test subject; where the headrest is located below the measurement axis, the contact element contacts a cheek of the test subject. In a known arrangement, the contact element is mounted at the front end of a threaded adjustment spindle extending parallel to the measurement axis, a rotary knob is mounted at a rear end of the spindle, and the spindle is mated in a threaded sleeve fixed to the instrument, whereby an extension distance of the contact element beyond the front of the instrument may be adjusted (i.e. extended and retracted) by rotation of the knob.

Headrests of the type described above are helpful, but they suffer a drawback. If the extension distance of the headrest contact element is set too large, proper positioning of the instrument is prevented because the instrument will be too far away from the eye of the test subject, and the measurement will result in an error message such as "too far." Conversely, if the extension distance of the headrest contact element is set too small, proper positioning of the instrument is prevented because the instrument will be too near to the eye of the test subject, and the measurement will result in an error message such as "too near." As a result, the operator must adjust the headrest and retake measurements until the instrument position is correct. Even if the extension distance is properly set, if the contact element is placed too far to the left or right on the forehead or cheek, or too high or low on the forehead or cheek, the operator must move the instrument away from the test subject's face before repositioning the contact element to achieve proper alignment. In summary, state of the art headrests do not facilitate fine positioning adjustments of the instrument in the X, Y, and/or Z directions while the contact element of the headrest remains in contact with the face of the test subject.

SUMMARY OF THE DISCLOSURE

The present disclosure provides a headrest for an ophthalmic instrument that facilitates fine positioning of the instrument relative to an eye of a test subject without the need to remove a contact element of the headrest from contact with the test subject's face. The ophthalmic instrument may be, for example, a rebound tonometer which propels a probe along a measurement axis of the instrument toward the eye, or a non-contact tonometer which discharges a fluid pulse along a measurement axis of the instrument toward the eye.

In an embodiment of the disclosure, an ophthalmic instrument for measuring an ophthalmic parameter of an eye of a test subject generally comprises a measurement axis and a headrest spaced vertically from the measurement axis, wherein the headrest includes a hollow bulbous contact element formed of resiliently deformable material, for example a thermoplastic elastomer (TPE) or silicone rubber. An outer surface of the contact element may have a spherical shape or a spheroidal shape when the contact element is not deformed.

In an embodiment of the disclosure, the headrest may include a base and a retainer, and the contact element may have a circumferential mounting portion which is received and captured between the base and the retainer. The retainer may be attached to the base by snap-fitted engagement with the base.

The hollow bulbous contact element may remain in contact with the patient's face and undergo reversible deformation as the operator makes fine positioning adjustments of the instrument relative to the eye in the three spatial dimensions X, Y, and Z.

BRIEF DESCRIPTION OF THE DRAWING VIEWS

The nature and mode of operation of the present invention will now be more fully described in the following detailed description taken with the accompanying drawing figures, in which.

Figure 4A:
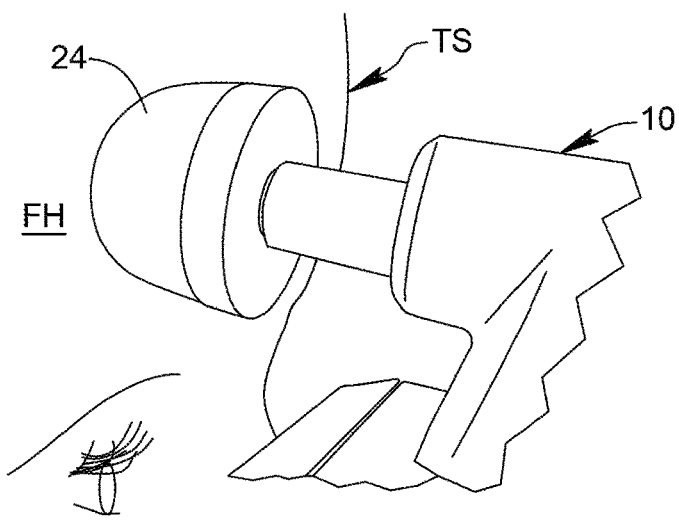
Figure 4B:
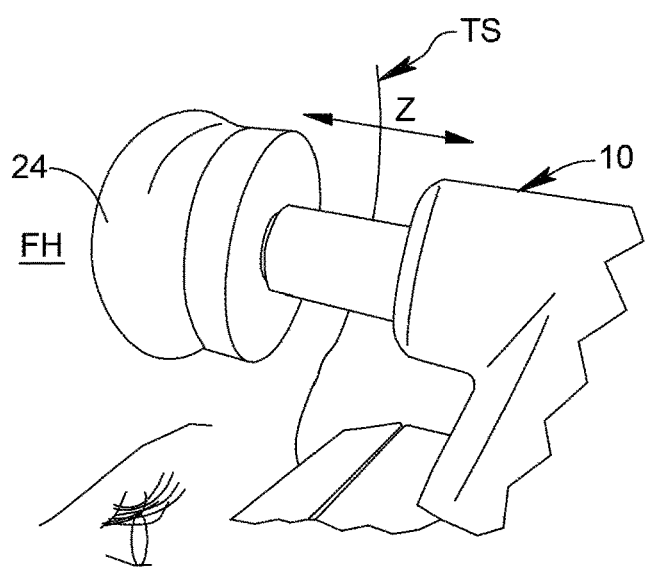
Figure 5:
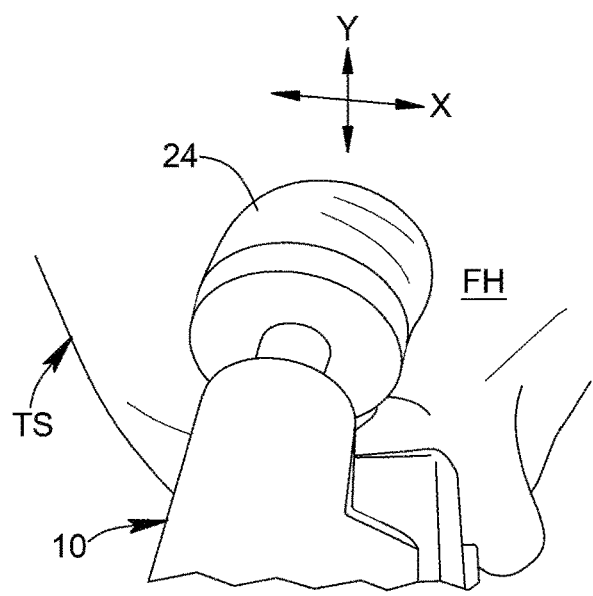

FIGS. 4A and 4B are perspective views showing flexible compliance of the contact element of the headrest as a working distance of the ophthalmic instrument is adjusted relative to the eye of the test subject; and FIG. 5 is another perspective view showing flexible compliance of the contact element of the headrest as the ophthalmic instrument is positioned laterally and vertically relative to the eye of the test subject.

DETAILED DESCRIPTION OF THE INVENTION

Figure 1:
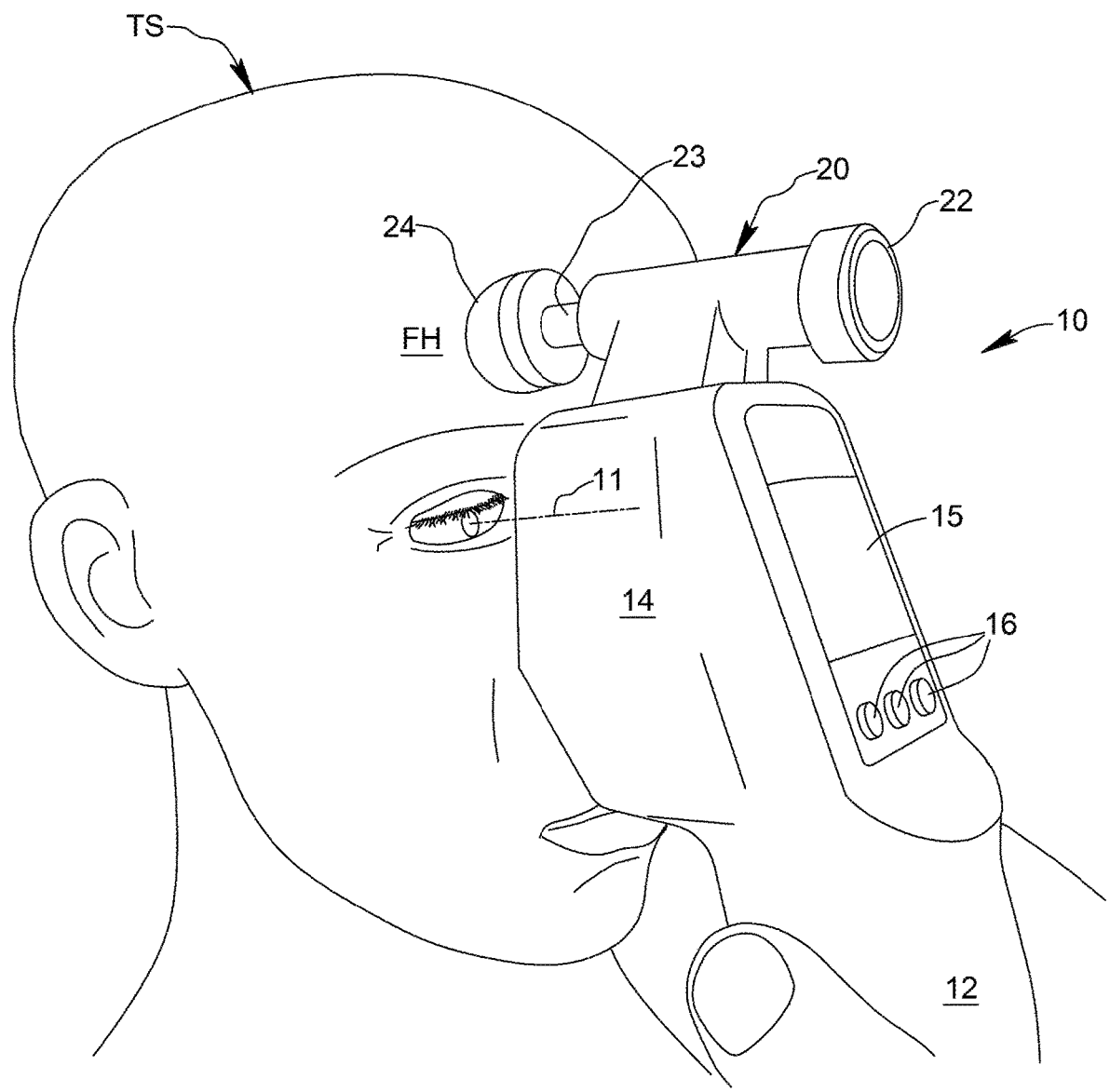
FIG. 1 is a perspective view showing an ophthalmic instrument having a flexible headrest formed in accordance with an embodiment of the present disclosure, wherein an operator is positioning the ophthalmic instrument relative to an eye of a test subject to take a measurement.

FIG. 1 shows an ophthalmic instrument 10 for measuring an ophthalmic parameter of an eye in accordance with an embodiment of the present disclosure. In the figures, ophthalmic instrument 10 is embodied as a rebound tonometer for measuring IOP of a test subject TS, however it is understood that ophthalmic instrument 10 may be embodied as a non-contact tonometer for measuring IOP, or may be embodied as another type of ophthalmic instrument for measuring a parameter of the eye other than IOP. Ophthalmic instrument 10 comprises a measurement axis 11. In the context of the illustrated rebound tonometer, measurement axis 11 is an axis along which a measurement probe (not shown) is propelled toward an eye of a test subject. In the context of a non-contact tonometer, measurement axis 11 is an axis of a fluid discharge tube through which a fluid pulse, e.g. an air puff, is directed at an eye of a test subject TS.

Ophthalmic instrument 10 may comprise a handle 12 and a measurement head 14 atop the handle 12. A measurement button (not shown) may be provided on handle 12 for initiating a measurement. Ophthalmic instrument 10 may also comprise a display 15 for presenting information to an operator, and menu navigation/selection buttons 16 enabling operator input. For example, display 15 may be used to display positioning guidance images to an operator in real time to help guide the operator in positioning ophthalmic instrument 10 relative to a test subject's eye for a taking a measurement. Display 15 may also be used to present control menus, measurement results, test subject data, and other information to an operator.

Ophthalmic instrument 10 further comprises a headrest 20 supported by measurement head 14. Headrest 20 may include an adjustment knob 22 mounted at a rear end of an adjustment spindle 23 and a contact element 24 mounted at a front end of the adjustment spindle 23.

Figure 2:
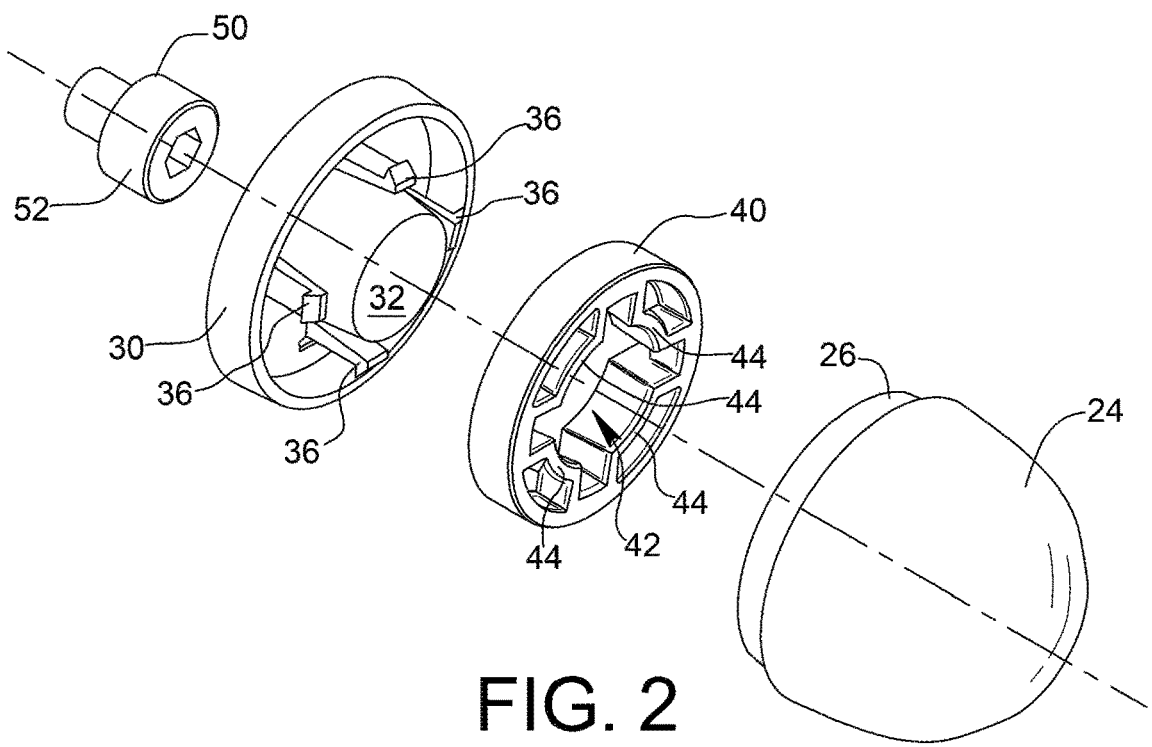
FIG. 2 is an exploded perspective view of showing a contact element of the flexible headrest and structure for mounting the contact element on an adjustment spindle of the headrest.
Figure 3:
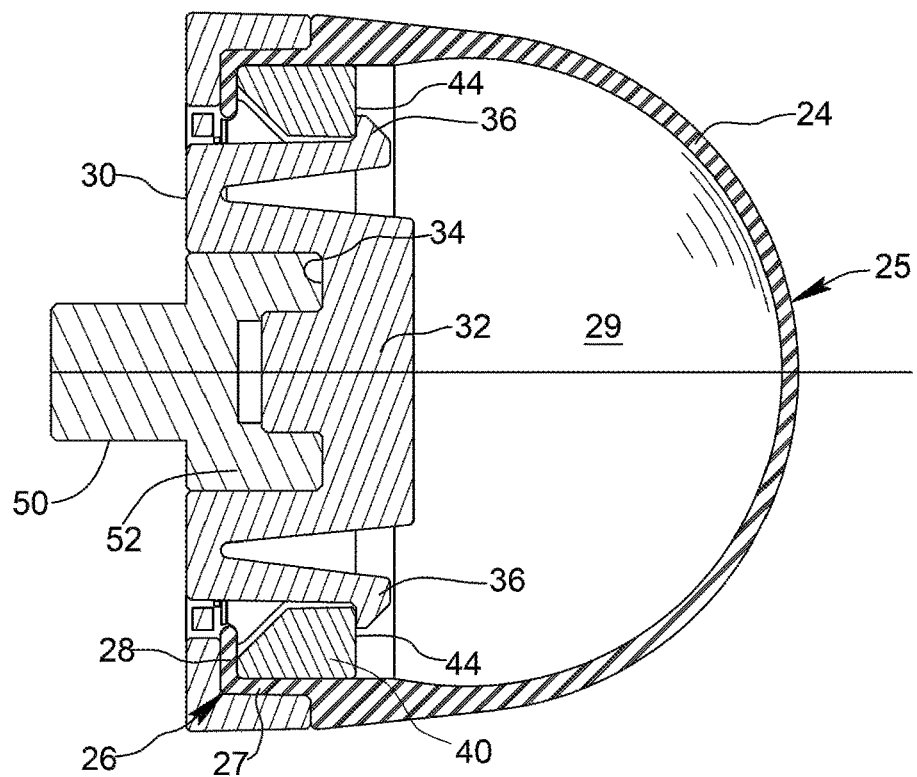
FIG. 3 is a cross-sectional view of the contact element and mounting structure shown in FIG. 2.

FIGS. 2 and 3 show contact element 24 and structure for mounting the contact element on adjustment spindle 23 in greater detail. As may be seen, contact element 24 is a hollow bulbous element. Contact element 24 is formed of resiliently deformable material. For example, contact element 24 may be formed of a thermoplastic elastomer (TPE), such as Versaflex OM 1040X-9 durometer 40A. Other brands, grades, and types of TPE may be used to form contact element 24. Of course, resiliently deformable materials other than TPE, for example silicone rubber, may be used to form contact element 24. Because contact element 24 makes contact with the skin of a test subject, it is beneficial to form contact element 24 from a material which is biocompatible, hypoallergenic, and easily cleaned and sterilized.

As can be seen in FIGS. 2 and 3, an outer surface 25 of contact element 24 may have a spherical shape or a spheroidal shape when the contact element 24 is not deformed. Contact element 24 may be sized to provide a comfortable and stable surface-to-surface contact area with the forehead FH of test subject TS when instrument 10 is moved closer to the eye such that a contacting portion of outer surface 25 conforms to the forehead of the test subject. By way of non-limiting example, outer surface 25 of contact element 24 may be spherically shaped to have a radius of curvature in a range from nine millimeters through eleven millimeters over a front portion of contact element 24. In one embodiment, the radius of curvature is about ten millimeters.

Headrest 20 further comprises structure for mounting contact element 24 on an end of adjustment spindle 23. For example, headrest may include a base 30, a retainer 40, and a threaded fastener 50 for mounting contact element 24 on adjustment spindle 23. Contact element 24 may have a circumferential mounting portion 26 received and held between base 30 and retainer 40. In the illustrated embodiment, mounting portion 26 of contact element 24 includes a cylindrical rim 27 and a flange 28 extending radially from the cylindrical rim 27, wherein the cylindrical rim 27 and the flange 28 are each held between base 30 and retainer 40. Base 30 and retainer 40 may be monolithic molded plastic parts. Retainer 40 may be attached to base 30 by snap-fitted engagement with base 30. For example, base 30 may include a plurality of resiliently deflectable catch-arms 36 angularly spaced about a central axis of base 30 and arranged to deflect through a central opening 42 in retainer 40 as base 30 and retainer 40 are brought together coaxially until respective barbed ends of the catch-arms snap into engagement with corresponding ledges 44 of retainer 40, thereby preventing withdrawal of retainer 40. As will be understood from FIG. 3, circumferential mounting portion 26 of contact element 24 is securely pinched between base 30 and retainer 40 upon assembly of the base and retainer.

Threaded fastener 50 may be attached to a rear portion of base 30 so that the entire assembly, including contact element 24, may be mounted at the front end of adjustment spindle 23 by mating fastener 50 in a threaded hole (not shown) in the front end of the adjustment spindle. Threaded fastener 50 may be attached to base 30 in any suitable manner. For example, in an embodiment shown in the figures, embodiment base 30 has a central hub 32 comprising a recess 34, and threaded fastener 50 includes a head portion 52 received and retained in the recess 34 of the central hub 32. Head portion 52 may be press-fitted into recess 34 and/or affixed in the recess by adhesive.

FIGS. 4A, 4B, and 5 illustrate use of ophthalmic instrument 10 having headrest 20 to measure ophthalmic parameters of an eye of test subject TS. FIGS. 4A and 4B show flexible compliance of contact element 24 to forehead FH as a working distance of ophthalmic instrument 10 is adjusted relative to the eye of test subject TS. In FIG. 4A, ophthalmic instrument 10 is just making contact with forehead FH. As ophthalmic instrument 10 is moved closer to forehead FH in FIG. 4B to reduce the Z-axis working distance, contact element 24 compresses in a reversible manner to accommodate the fine position adjustment.

FIG. 5 shows flexible compliance of contact element 24 as ophthalmic instrument 10 is positioned laterally and vertically relative to the eye of test subject TS. In the representative view of FIG. 5, ophthalmic instrument 10 is being moved slightly downward (Y-axis) and to the left (X-axis), and contact element 24 reversibly deforms to accommodate the fine position adjustment while maintaining contact with forehead FH.

Although the embodiment of ophthalmic instrument 10 illustrated in the figures shows headrest 20 located above measurement axis 11 for contact with forehead FH of test subject TS, those skilled in the art will recognize that headrest 20 may be arranged below measurement axis 11 for contact with a cheek of test subject TS.

The present disclosure provides a headrest for an ophthalmic instrument that facilitates fine positioning of the instrument relative to an eye of a test subject and is comfortable to the test subject. The headrest of the present disclosure greatly reduces the need to remove the contact element of the headrest from contact with the test subject's face to reposition the contact element on the face and/or adjust an extension/retraction position of the contact element relative to the measurement head of the instrument. As a result, measurement efficiency and the test subject experience are improved.

While the present disclosure describes exemplary embodiments, the detailed description is not intended to limit the scope of the appended claims to the particular embodiments set forth. The claims are intended to cover such alternatives, modifications and equivalents of the described embodiments as may be included within the scope of the claims.

What is claimed is:

1. An ophthalmic instrument (10) for measuring an ophthalmic parameter of an eye of a test subject, the ophthalmic instrument (10) comprising:
   a measurement axis (11); and
   a headrest (20) spaced vertically from the measurement axis (11), wherein the headrest (20) includes a hollow bulbous contact element (24) formed of resiliently deformable material;
   wherein the headrest (20) further includes a base (30) and a retainer (40), and the contact element (24) has a circumferential mounting portion (26), wherein the mounting portion (26) of the contact element (24) is received between the base (30) and the retainer (40);
   wherein the retainer (40) is a monolithic part and the base (30) is another monolithic part, and the base (30) and the retainer (40) are attached to each other by direct snap-fitted engagement of the retainer (40) with the base (30); and
   wherein the base (30) has a central hub (32) comprising a recess (34), and the headrest further includes a threaded fastener (50) having a head portion (52) received in the recess (34) of the central hub (32).

2. The ophthalmic instrument (10) according to claim 1, wherein an outer surface (25) of the contact element (24) has a spherical shape or a spheroidal shape when the contact element (24) is not deformed.

3. The ophthalmic instrument (10) according to claim 2, wherein the outer surface (25) of contact element (24) has a spherical shape with a radius of curvature in a range from nine millimeters through eleven millimeters.

4. The ophthalmic instrument (10) according to claim 3, wherein the radius of curvature is about ten millimeters.

5. The ophthalmic instrument (10) according to claim 1, wherein the resiliently deformable material is a thermoplastic elastomer (TPE) or silicone rubber.

6. The ophthalmic instrument (10) according to claim 1, wherein the mounting portion (26) of the contact element (24) includes a cylindrical rim (27) and a flange (28) extending radially from the cylindrical rim (27), wherein the cylindrical rim (27) and the flange (28) are each held between the base (30) and the retainer (40).

7. The ophthalmic instrument (10) according to claim 1, wherein the head portion (52) of the threaded fastener (50) is press-fitted into the recess (34) of the central hub (32).

* * * * *